United States Patent [19]

Werner et al.

[11] 4,265,833

[45] May 5, 1981

[54] PROCESS FOR THE PREPARATION OF HYDROXY-DIPHENYLAMINES

[75] Inventors: Friedrich Werner, Cologne; Heinz U. Blank, Odenthal, both of Fed. Rep. of Germany

[73] Assignee: Bayer Aktiengesellschaft, Leverkusen, Fed. Rep. of Germany

[21] Appl. No.: 91,625

[22] Filed: Nov. 5, 1979

[30] Foreign Application Priority Data

Nov. 21, 1978 [DE] Fed. Rep. of Germany ....... 2850391

[51] Int. Cl.$^3$ .................... C07C 85/06; C07C 121/64; C07C 137/00; C07C 101/04
[52] U.S. Cl. ................ 564/435; 260/456 A; 260/456 P; 260/465 E; 560/19; 560/139; 560/141; 560/142; 562/433

[58] Field of Search ............... 260/571, 576, 577, 582, 260/465 E, 456 A; 560/19, 139; 562/433

[56] References Cited

U.S. PATENT DOCUMENTS 3,450,764    6/1969    Altwicker ........................... 260/571

Primary Examiner—John Doll
Attorney, Agent, or Firm—Sprung, Felfe, Horn, Lynch & Kramer

[57] ABSTRACT

A process for the preparation of hydroxy-diphenylamines by condensation of dihydroxybenzene with an excess amount of primary aromatic amine in the presence of a catalytic amount of an acid at elevated temperature is described wherein the excess aromatic amine and, if appropriate, the reaction product is distilled off from the reaction mixture in the presence of a base.

4 Claims, No Drawings

PROCESS FOR THE PREPARATION OF HYDROXY-DIPHENYLAMINES

The invention relates to a process for the preparation of optionally substituted hydroxy-diphenylamines by condensation of an optionally substituted dihydroxybenzene with an optionally substituted primary aromatic amine.

It is known from U.S. Pat. No. 3,450,764 to subject dihydroxybenzenes to condensation reactions with primary aromatic amines in the presence of para-toluenesulphonic acid to give diarylamines. This process requires 9 to 18% of para-toluenesulphonic acid, relative to the dihydroxybenzene, and has the technological disadvantage that the entire sulphonic acid must be isolated by expensive extraction before the reaction product is isolated.

A process has been found for the preparation of hydroxy-diphenylamines by condensation of a dihydroxybenzene with an excess of a primary aromatic amine in the presence of catalytic amounts of an acid at elevated temperature, which is characterized in that when the condensation reaction has ended, the excess primary aromatic amine and if appropriate the reaction product are distilled off from the reaction mixture in the presence of a base.

Examples of dihydroxybenzenes which can be employed in the process according to the invention are those of the formula (I)

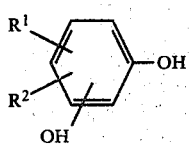
(I)

in which
R$^1$ and R$^2$ can be identical or different and represent hydrogen, halogen, alkyl, cycloalkyl, alkoxy, phenyl, phenyloxy, cyano, the carboxyl group, alkoxycarbonyl, alkylcarbonyloxy, alkylcarbonyl or the sulphonic acid ester group,
and wherein, in addition to the meaning given,
R$^1$ and R$^2$, if they are adjacent, can together form a fused cycloaliphatic or aromatic ring. Dihydroxybenzene of the formula (I)
in which
R$^1$ and R$^2$ can be identical or different and represent hydrogen, halogen, alkyl, alkoxy, phenyl or phenyloxy, or, if they are adjacent, can together form a fused aromatic ring,
can preferably be employed in the process according to the invention.
Phenols of the formula (I)
in which
R$^1$ and R$^2$ can be identical or different and represent hydrogen, halogen, alkyl or alkoxy, or, if they are adjacent, can together form a fused aromatic ring,
can particularly preferably be employed in the process according to the invention.

Examples of primary aromatic amines which can be employed in the process according to the invention are those of the formula (II)

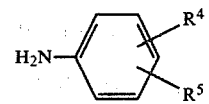
(II)

in which
R$^4$ and R$^5$ can be identical or different and represent hydrogen, halogen, alkyl, cycloalkyl, alkoxy, phenyl, phenyloxy, cyano, the carboxyl group, alkoxycarbonyl, alkylcarbonyloxy, alkylcarbonyl or the sulphonic acid ester group,
and wherein, additionally,
R$^4$ and R$^5$, if they are adjacent, can together form a fused cycloaliphatic or aromatic ring. Amines of the formula (II)
in which
R$^4$ and R$^5$ can be identical or different and represent hydrogen, halogen, alkyl or alkoxy,
and wherein, additionally,
R$^4$ and R$^5$, if they are adjacent, can together form a fused aromatic ring,
can preferably be employed in the process accordng to the invention.

Examples of halogen which may be mentioned are fluorine, chlorine or bromine, preferably chlorine.

Examples of alkyl which may be mentioned are straight-chain or branched alkyl radicals with 1 to 4 carbon atoms, such as methyl, ethyl, propyl, isopropyl, butyl or isobutyl. Preferred alkyl is methyl or ethyl. Particularly preferred alkyl is the methyl radical.

Examples of cycloalkyl which may be mentioned are carbocyclic systems with 5 to 7 ring members, which can optionally be substituted by lower alkyl, such as cyclopentyl, methyl-cyclopentyl, cyclohexyl, methyl-cyclohexyl, cycloheptyl or methyl-cycloheptyl. Preferred cycloalkyl are the cyclopentyl ring and the cyclohexyl ring.

Examples of alkoxy which may be mentioned are radicals which are derived from a lower alcohol with 1 to 4 carbon atoms, such as methoxy, ethoxy, propoxy, isopropoxy, butoxy or isobutoxy. Preferred alkoxy is the methoxy radical.

Examples of alkoxycarbonyl which may be mentioned are those radicals, the ester group of which is derived from a lower alcohol with 1 to 4 carbon atoms, such as the methyl ester, ethyl ester, propyl ester or butyl ester of a carboxylic acid.

Examples of alkylcarbonyloxy which may be mentioned are a hydroxyl group esterified by a C$_1$–C$_4$-carboxylic acid, such as a hydroxyl group esterified by formic acid, acetic acid, propionic acid or butyric acid.

Examples of alkylcarbonyl which may be mentioned are acyl groups with 2 to 5 carbon atoms, such as acetyl, propionyl, butyryl or valeroyl.

Examples of a sulphonic acid ester group which may be mentioned are those which are derived from a lower alcohol with 1 to 4 carbon atoms, such as the sulphonic acid methyl ester, ethyl ester, propyl ester or butyl ester.

The radicals R$^1$ and R$^2$ and the radicals R$^4$ and R$^5$, if they are adjacent, can independently of one another denote a fused cycloaliphatic or aromatic ring. The fused cycloaliphatic ring can be, for example, a 5-membered or 6-membered ring. In this manner, it is possible to pass from the benzene series into the indane series, the tetrahydronaphthalene series and the naphthalene series.

Examples which may be mentioned of dihydroxybenzenes which can be employed in the process according to the invention are: pyrocatechol, resorcinol, hydroquinone, alkyl-substituted pyrocatechol, alkyl-substituted resorcinol, alkyl-substituted hydroquinone, chlorine-substituted pyrocatechol, chorine-substituted resorcinol, chlorine-substituted hydroquinone, 1,2-, 1,3-, 1,4-, 1,5-, 1,6-, 1,7- and 1,8-dihydroxy-naphthalene, alkyl-substituted 1,2-, 1,3-, 1,4-, 1,5-, 1,6-, 1,7- and 1,8-dihydroxy-naphthalene, 2,3- dihydroxy-benzoic acid, 2,4-dihydroxy-benzoic acid, 2,5- dihydroxy-benzoic acid, 2,3-dihydroxy-benzoic acid methyl ester, 2,4-dihydroxy-benzoic acid ethyl ester, 2,5-dihydroxy-benzoic acid butyl ester and 2,3-, 2,4- and 2,5-dihydroxy-diphenyl.

Examples which may be mentioned of primary aromatic amines which can be employed in the process according to the invention are: aniline, o-, m- and p-chloroaniline, o-, m- and p-bromoaniline, o-, m- and p-toluidine, o-, m- and p-cyclohexyl-aniline, o-, m- and p-methoxy-aniline, o-, m- and p-phenyl-aniline, o-, m- and p-phenyloxy-aniline, 1-naphthylamine and 2-naphthylamine.

The primary aromatic amine is employed in a molar excess, relative to the phenol employed, in the process according to the invention. A ratio of 1.1 to 10 mols of primary aromatic amine per 1 mol of phenol, for example, may be mentioned for this process. The preferred ratio is 1.1 to 7 mols of primary aromatic amine, and very particularly preferably 1.2 to 5 mols of primary aromatic amine, per 1 mol of phenol.

The condensation reaction in the process according to the invention is carried out in the presence of an acid of the formula (III)

$$R^6\text{—}SO_3H \tag{III}$$

in which
$R^6$ represent alkyl, cycloalkyl, aryl or hydroxyl.

An example of alkyl ($R^6$) which may be mentioned is a straight-chain or branched aliphatic hydrocarbon radical with 1 to 18 carbon atoms, such as methyl, ethyl, propyl, isopropyl, butyl, isobutyl, hexyl, isohexyl, octyl, isodecyl, dodecyl, palmityl or stearyl.

An example of cycloalkyl ($R^6$) which may be mentioned is optionally alkyl-substituted cyclopentyl, cyclohexyl or cycloheptyl.

An example of aryl ($R^6$) which may be mentioned is an optionally substituted aromatic radical from the benzene or naphthalene series, such as phenyl, toluyl, 1-naphthyl or 2-naphthyl.

Examples which may be mentioned of acids which can be employed in the process according to the invention are: methylsulphonic acid, ethylsulphonic acid, benzenesulphonic acid, p-toluenesulphonic acid, 1-naphthyl-sulphonic acid, 2-naphthyl-sulphonic acid and sulphuric acid.

The acid of the formula (III) can be employed in the process according to the invention in a catalytic amount. An amount which may be mentioned is 1 to 10% by weight, preferably 2 to 5% by weight, relative to the amount of phenol employed.

The condensation reaction in the process according to the invention can be carried out in a temperature range from 150° to 250° C., preferably in the temperature range from 180° to 220° C. The condensation reaction in the process according to the invention is very particularly preferably carried out at the boiling point of the lowest-boiling reaction component.

The condensation reaction in the process according to the invention can be carried out under normal pressure. It is, of course, also possible to carry out the reaction under increased pressure, for example, in order to keep low-boiling reactants in the liquid state of aggregation. A pressure of up to 10 bars may be mentioned for this. The reaction is preferably carried out under the autogenous pressure of the reaction component which is established at the desired reaction temperature.

The condensation reaction in the process according to the invention can be carried out without solvents. It is, of course, also possible to carry out the reaction in the presence of a solvent which is inert with respect to the condensation reaction. Examples which may be mentioned of suitable solvents are: aliphatic and aromatic hydrocarbons, such as high-boiling benzine fractions or diphenyl, chlorinated hydrocarbons, such as dichloro-benzenes, diphenyl ether, sulphones and substituted and unsubstituted acid amides.

The water formed during the condensation reaction in the process according to the invention can be distilled off continuously. In the case where the reaction is carried out in the presence of a solvent, this distillation can take place in the form of an azeotropic distillation. However, the water formed can also be removed from the reaction mixture with the aid of a weak stream of inert gas through the reaction mixture. An example of an inert gas which may be mentioned is nitrogen, argon or carbon dioxide.

When the condensation reaction has ended, the reaction mixture can be worked up according to the invention by distillation in the presence of a base. Examples of bases which may be mentioned are the hydroxides and carbonates of the alkali metals or alkaline earth metals, such as sodium hydroxide, potassium hydroxide, sodium carbonate, potassium carbonate, magnesium hydroxide, calcium hydroxide, magnesium carbonate or calcium carbonate.

The base can be employed in the solid or dissolved form, if the compounds are soluble. In the case of soluble bases, concentrated aqueous solutions thereof are preferably used. Sodium hydroxide in the form of concentrated sodium hydroxide solution is preferably employed as the base.

It is, of course, also possible to employ organic bases in the process according to the invention if they are not volatile under the distillation conditions.

The base is added in an amount which is sufficient to neutralize the acid present in the reaction mixture. of course, it is possible to carry out the inventive process in the presence of less alkali than is sufficient to neutralize the acid but some unwanted by-products may occur in this case and lower the yield. If more alkali is used than is sufficient to neutralize the acid the residue in the distillation sump will be increased whereby the danger of an incrustation becomes greater. Furthermore, the unnecessary alkali causes additional costs.

In general, from 0.7 to 1.5 equivalents of the said alkali per 1 equivalent of the acid of the formula (III) are employed. Preferably from 0.9 to 1.3, particularly preferred from 1.0 to 1.2 equivalents of the said alkali per 1 equivalent of the said acid are employed. The base to be employed according to the invention can be added before the start of the distillative separation of the distillation mixture. However, it is also possible to add the base to the reaction mixture whilst distilling off the primary aromatic amine employed in excess.

After distilling off the excess primary aromatic amine, the optionally substituted hydroxy-diphenylamine formed as the reaction product can be isolated, for example by distillation from the residue which remains or by recrystallisation.

Optionally substituted hydroxy-diphenylamines of the

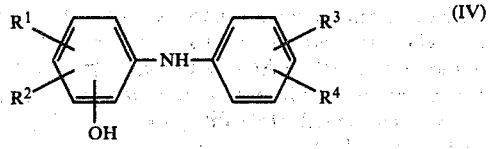

in which $R^1$ to $R^4$ have the abovementioned meaning, can be prepared in the process according to the invention.

Examples which may be mentioned of compounds of the formula (IV) are: 2-hydroxy-diphenylamine, 3-hydroxy-diphenylamine, 4-hydroxy-diphenylamine, 2-hydroxy-4-methyl-diphenylamine, 3-hydroxy-4-chloro-diphenylamine, 2-cyclohexyl-4-hydroxy-diphenylamine, 3-hydroxy-4-ethoxy-diphenylamine, 2-hydroxy-3-phenyl-diphenylamine, 3-hydroxy-5-cyano-diphenylamine, 3-hydroxy-diphenylamine-5-carboxylic acid methyl ester, 2-hydroxy-diphenylamine-4-sulphonic acid methyl ester, 3-hydroxy-2'-methyl-diphenylamine, 3-hydroxy-2'-chloro-diphenylamine, 3-hydroxy-4'-methoxy-diphenylamine, 3-hydroxy-4'-methyl-diphenylamine, 2-hydroxy-4-phenyldiphenylamine-4'-sulphonic acid methyl ester, 3-hydroxy-3-methoxy-5,5'-dicyano-diphenylamine, 1-(3-hydroxy-naphthyl)-1-naphthyl-amine, 1-(2-hydroxy-naphthyl)-4-methoxy-phenylamine, 1-(3-hydroxy-5,6,7,8-tetrahydro-naphthyl)-phenylamine and 4-hydroxy-phenyl-1-naphthyl-amine.

The process according to the invention enables optionally substituted diphenylamines to be prepared in a technically advanced manner. It is distinguished by a technologically simple procedure and high space/time yields.

It is surprising that the process according to the invention gives, with simple technological measures, almost quantitative yields, relative to phenol employed.

3-Hydroxy-diphenylamine, mixed with 4-chloro-2-aminophenol, can be used for dyeing, for example, furs, hair and feathers (German Reichspatent No. 334,011). Dye-stuffs of the rhodamine series can be prepared by condensation of 2-methyl-3-hydroxy-diphenylamine with phthalic anhydride in the presence of sulphuric acid (German Reichspatent No. 450,820). Furthermore, the potassium salt of optionally substituted 3-hydroxy-diphenylamine can be reacted with carbon dioxide to give the corresponding 3-hydroxy-diphenylamine-carboxylic acids which are valuable dyestuff intermediates. (German Reichspatent No. 515,208). Furthermore, an optionally substituted 2-chloro-3'-hydroxydiphenylamine can be reacted with aqueous alkali at elevated temperature to yield the corresponding optionally substituted 2-hydroxy-carbazole (DE-OS/German Published Specification) 2,711,943)which can be converted into the 2-hydroxy-carbazole-3-carboxylic acid by reaction with carbon dioxide in the presence of sodium hydroxide and transferred to the 2-hydroxy-carbazole-3-carboxylic acid anilide by known means. The latter can be coupled in an alkaline solution with various diazotized aromatic amines, for example dichloro aniline, nitro-anisidine or amino-carbazole, to yield azo dyes which are insoluble in water and have a high fastness to light (DRP (German Reichspatent) No. 551,880).

EXAMPLE 1

1,651.6 g (15 mols) of resorcinol are stirred with 5,740.6 g (45 mols) of o-chloroaniline and 66.1 g of p-toluenesulphonic acid at 180° C. for 18 hours. 84 g of o-chloroaniline and 270 g (15 mols) of $H_2O$ thereby pass over in a weak $N_2$ stream (10 liters/hour$^{-1}$). 34.2 g of 45% strength sodium hydroxide solution=15.4 g of 100% pure sodium hydroxide are added dropwise to the warm solution. Excess chloroaniline is then distilled off under 1 mbar. 3,405 g of 96.7% pure 2-chloro-3'-hydroxydiphenylamine=100% of theory are obtained. The content was determined by gas chromatography in accordance with the internal standard method.

COMPARISON EXAMPLE 2 AND EXAMPLES 3 TO 13

The following examples were obtained analogously to Example 1:

| Ex. | Amount employed (g) Resorcinol | o-Chloro-aniline | Molar ratio | toluene-sulphonic acid (g) | Temperature °C. |
|---|---|---|---|---|---|
| 2 | 1,651.6 | 5,740.6 | 1:3 | 66.1 | 180 |
| 3 | 1,651.6 | 5,740.6 | 1:3 | 66.1 | 180 |
| 4 | 552.0 | 1,278.0 | 1:2 | 22.0 | 180 |
| 5 | 552.0 | 767.0 | 1:1.2 | 22.0 | 180 |
| 6 | 552.0 | 1,918.0 | 1:3 | 22.0 | 190 |
| 7 | 552.0 | 1,278.0 | 1:2 | 22.0 | 190 |
| 8 | 552.0 | 960.0 | 1:1.5 | 22.0 | 190 |
| 9 | 552.0 | 767.0 | 1:1.2 | 22.0 | 190 |
| 10 | 552.0 | 1,918.0 | 1:3 | 22.0 | 200 |
| 11 | 552.0 | 1,278.0 | 1:2 | 22.0 | 200 |
| 12 | 552.0 | 960.0 | 1:1.5 | 22.0 | 200 |
| 13 | 552.0 | 767.0 | 1:1.2 | 22.0 | 200 |

| Ex. | Sodium hydroxide solution (g) | Time (hours) | $H_2O$ formed (g) | 2-Chloro-3'-hydroxy diphenyl-amine (g) | Content (%) | Yield (% of theory) |
|---|---|---|---|---|---|---|
| 2 | — | 18 | 270 | 3,406.0 | 82.2 | 85.0 |
| 3 | 15.4 | 18 | 270 | 3,405.0 | 96.7 | 100.0 |
| 4 | 5.1 | 13 | 85 | 1,129.2 | 96.0 | 98.8 |
| 5 | 5.1 | 20 | 87 | 1,088.3 | 82.2 | 81.5 |
| 6 | 5.1 | 7 | 88 | 1,125.6 | 97.5 | 99.3 |
| 7 | 5.1 | 5.5 | 90 | 1,128.0 | 94.7 | 97.3 |
| 8 | 5.1 | 7.5 | 90 | 1,123.0 | 87.8 | 89.8 |
| 9 | 5.1 | 4 | 86 | 1,080.0 | 88.5 | 87.0 |
| 10 | 5.1 | 4 | 90 | 1.096.2 | 98.5 | 100.0 |
| 11 | 5.1 | 4 | 83 | 1,128.6 | 91.6 | 94.2 |
| 12 | 5.1 | 2.5 | 87 | 1,116.2 | 88.2 | 89.6 |
| 13 | 5.1 | 2.5 | 88 | 1,076.7 | 85.2 | 83.5 |

EXAMPLE 14

330 g (3 mols) of resorcinol are stirred with 1,107 g (9 mols) of 4-methoxyaniline and 13.2 g of p-toluenesulphonic acid at 200° C. for 18 hours. 54 g of water thereby distil off. The mixture is allowed to cool to 80° C. and 6.9 g of 45% strength sodium hydroxide solution are stirred in. Excess 4-methoxyaniline is then distilled off. 658 g of 3-hydroxy-4'-methoxy-diphenylamine are obtained with a purity of 95% (=96.9% of the theoretical yield).

EXAMPLE 15

275 g (2.5 mols) of resorcinol are stirred with 1,027.5 g (7.5 mols) of 3-methoxy-4-methylaniline and 110 g of p-toluenesulphonic acid at 200° C. for 21 hours. 45 g of $H_2O$ thereby distil off. After cooling the mixture to 70° C., 5.8 g of 45% strength sodium hydroxide solution are stirred in and the excess 3-methoxy-4-methylaniline is distilled off. 584 g of 3-hydroxy-3'-methoxy-4'-methyl-diphenylamine are obtained with a purity of 93.5% (=95.4% of the theoretical yield).

EXAMPLE 16

1,100 g (10 mols) of resorcinol are stirred with 3,214.5 g (30 mols) of o-toluidine and 44 g of p-toluenesulphonic acid at 200° C. for 18 hours. 180 g of $H_2O$ thereby distil off. After cooling the mixture, 20.5 g of 45% strength sodium hydroxide solution are stirred in and excess o-toluidine is distilled off. 2,030 g of 2-methyl-3-hydroxy-diphenylamine are obtained with a purity of 96% (=97.9% of the theoretical yield).

EXAMPLE 17

330.3 g (3 mols) of hydroquinone are heated to 175° C. together with 838 g (9 mols) of aniline and 13.2 g of p-toluenesulphonic acid, whilst stirring. As the reaction progresses, the temperature is increased up to 205° C. 56 g of $H_2O$ distil off in the course of 35 hours. The mixture is allowed to cool to 80° C. and 6.9 g of 45% strength by weight sodium hydroxide solution are stirred in. After distilling off the excess aniline, 567 g of 4-hydroxy-diphenylamine are obtained with a purity of 82.8% by weight; this corresponds to 87.5% of the theoretical yield.

What is claimed is:

1. A process for the preparation of a hydroxydiphenylamine which comprises condensing a dihydroxybenzene with an excess amount of a primary aromatic amine in the presence of a catalytic amount of an acid at an elevated temperature and, without isolating said acid, thereafter distilling off excess primary aromatic amine from the reaction mixture in the presence of a base.

2. A process according to claim 1 wherein said base is a hydroxide or carbonate of an alkali metal or alkaline earth metal.

3. A process according to claim 1 wherein said base is a concentrated sodium hydroxide solution.

4. A process according to claim 1 wherein said base is present in an amount sufficient to neutralize the acid present in the reaction mixture.

* * * * *